(12) United States Patent
Gao et al.

(10) Patent No.: US 11,382,673 B2
(45) Date of Patent: Jul. 12, 2022

(54) POWER PEDICLE SCREWDRIVER

(71) Applicant: Mako Surgical Corp., Fort Lauderdale, FL (US)

(72) Inventors: Xiao Hui Gao, Plantation, FL (US); Hyosig Kang, Weston, FL (US); Daryle Lee, Cooper City, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 84 days.

(21) Appl. No.: 16/738,053

(22) Filed: Jan. 9, 2020

(65) Prior Publication Data

US 2020/0138489 A1 May 7, 2020

Related U.S. Application Data

(62) Division of application No. 15/674,001, filed on Aug. 10, 2017, now Pat. No. 10,561,448.

(60) Provisional application No. 62/373,712, filed on Aug. 11, 2016.

(51) Int. Cl.
*A61B 17/70* (2006.01)
*A61B 34/30* (2016.01)
*B25F 5/00* (2006.01)
*A61B 17/88* (2006.01)
*A61B 17/00* (2006.01)
*A61B 17/56* (2006.01)

(52) U.S. Cl.
CPC ...... *A61B 17/7082* (2013.01); *A61B 17/8875* (2013.01); *A61B 34/30* (2016.02); *B25F 5/001* (2013.01); *A61B 2017/00398* (2013.01); *A61B 2017/00477* (2013.01); *A61B 2017/564* (2013.01); *A61B 2034/303* (2016.02)

(58) Field of Classification Search
CPC ...... A61B 17/7082; A61B 2017/00398; A61B 17/8875
See application file for complete search history.

(56) References Cited

U.S. PATENT DOCUMENTS

| 2,375,952 A | 5/1945 | Sinclair |
| 2,494,156 A | 1/1950 | Bechler |
| 2,727,402 A | 12/1955 | Thoresen |

(Continued)

FOREIGN PATENT DOCUMENTS

| EP | 709168 A1 | 5/1996 |
| WO | 2010128754 A1 | 11/2010 |

*Primary Examiner* — Julianna N Harvey
(74) *Attorney, Agent, or Firm* — Lerner, David, Littenberg, Krumholz & Mentlik, LLP

(57) ABSTRACT

Disclosed herein are gear shifters to reverse an output shaft rotation and a method for using the same. A gear shifter in accordance with the present invention may include a housing, an input shaft, an output shaft and an idler shaft. The input shaft may have input gears, the output shaft may have output gears and the idler shaft may have idler gears. The output shaft may be slidably coupled with the input shaft and the idler shaft to rotate in a first direction in a first position and in a second opposite direction in a second position. A method of reversing an output shaft direction using a gear shifter may include the steps of pushing the gear shifter in a first direction to rotate the output shaft in a first direction and pushing the gear shifter in a second direction to rotate the output shaft in a second direction.

20 Claims, 9 Drawing Sheets

(56) References Cited

U.S. PATENT DOCUMENTS

| | | | |
|---|---|---|---|
| 3,160,033 | A | 12/1964 | Moyer |
| 3,315,545 | A | 4/1967 | Schnoebelen |
| 3,812,736 | A | 5/1974 | Nickstadt |
| 3,851,537 | A | 12/1974 | Nickstadt |
| 4,217,964 | A | 8/1980 | Eaton |
| 4,366,871 | A | 1/1983 | Dieterle et al. |
| 4,484,871 | A | 11/1984 | Adman et al. |
| 4,573,370 | A | 3/1986 | Clemens |
| 5,931,062 | A | 8/1999 | Marcovici |
| 5,946,988 | A | 9/1999 | Metz-Stavenhagen |
| 6,044,733 | A | 4/2000 | Liu |
| 6,723,100 | B2 | 4/2004 | Biedermann et al. |
| 7,226,453 | B2 | 6/2007 | Chao et al. |
| 7,849,766 | B2 | 12/2010 | Sharifi-Mehr et al. |
| 8,016,836 | B2 | 9/2011 | Corrao et al. |
| 8,231,635 | B2 | 7/2012 | Sharifi-Mehr et al. |
| 8,394,108 | B2 | 3/2013 | McLean et al. |
| 8,747,238 | B2 | 6/2014 | Shelton, IV et al. |
| 8,784,431 | B1 * | 7/2014 | Harder ............... A61B 17/7082 606/104 |
| 8,926,637 | B2 | 1/2015 | Zergiebel |
| 9,295,500 | B2 | 3/2016 | Marigowda |
| 2005/0268750 | A1 | 12/2005 | Bruce et al. |
| 2008/0200918 | A1 | 8/2008 | Spitler et al. |
| 2010/0268284 | A1 | 10/2010 | Bankoski et al. |
| 2010/0298838 | A1 | 11/2010 | Walters |
| 2012/0031239 | A1 | 2/2012 | Hu et al. |
| 2012/0130388 | A1 | 5/2012 | Plotkin |
| 2013/0282031 | A1 * | 10/2013 | Woodard, Jr. ..... A61B 17/0625 606/147 |
| 2014/0324062 | A1 | 10/2014 | Heuer et al. |
| 2016/0206310 | A1 | 7/2016 | Shelton, IV |
| 2017/0181774 | A1 * | 6/2017 | Cahill ..................... B25B 15/02 |

\* cited by examiner

POWER PEDICLE SCREWDRIVER

CROSS-REFERENCE TO RELATED APPLICATION

The present application is a divisional of U.S. application Ser. No. 15/674,001, filed on Aug. 10, 2017, which claims the benefit of the filing date of U.S. Provisional Patent Application No. 62/373,712, filed on Aug. 11, 2016, the disclosures of all of which are hereby incorporated by reference in their entirety.

BACKGROUND OF THE INVENTION

The present invention relates to an apparatus and method for reversing an output shaft rotation, and in particular a reverse gear shifter and a method for reversing output shaft rotation of a powered tool during the insertion of a pedicle screw.

Power tools used in inserting and retracting fasteners are well known. For instance, drills or powered screw drivers are widely utilized in inserting and removing screws from substrates in carpentry and the like. These devices typically have a shaft that is designed to rotate in two directions (i.e., one for insertion and one for removal). The mechanisms for causing the different rotation vary. In some instances, multiple triggers are provided for causing the different directional rotation. In other cases, an actuator is provided that causes a single trigger to provide the different rotation.

Power tools are also widely utilized in orthopedic surgery, especially in connection with the insertion and removal of bone screws. For instance, pedicle screws are widely utilized in spinal fusion procedures. These screws typically include a bone screw portion and a tulip that is polyaxially associated therewith. During insertion, a driver tool is coupled to both of those components and the bone screw portion is driven into the pedicle of a vertebral body. Thereafter, the tool must be removed by imparting an opposite force upon the portion of the tool engaging the tulip while not imparting a similar force on the bone screw portion. This is typically achieved by disengaging the tool from the bone screw portion and operating the driver in a manner that allows for the opposition rotation on the portion engaging the tulip.

The tools utilized in pedicle screw insertion are often somewhat cumbersome to utilize and not intuitive for a surgeon. For instance, drivers may require actuation of one button for insertion of the pedicle screw and another button for disengagement of the tool therefrom. Given the advent of more user friendly tools for performing surgical procedures, such as the use of robots, there is a need for easy and intuitive tools for performing such procedures, for instance, in the insertion of pedicle screws.

BRIEF SUMMARY OF THE INVENTION

Disclosed herein are gear shifters for reversing an output shaft rotation and a method of using the same.

In a first aspect of the present invention, a gear shifter is provided. The gear shifter may have a housing, an input shaft, an output shaft and an idler shaft. The input shaft may have an input gear and a first side of the input shaft may be within the housing and a second side of the input shaft may extend from the housing. The output shaft may have an output gear and a first side of the output shaft may be within the housing and a second side of the output gear may extend from the housing. The idler shaft may have an idler gear. The output shaft may be slidably coupled with the input shaft to rotate in an opposite direction of the input shaft when the housing is in a first position, and the output shaft may be slidably coupled with the idler shaft to rotate in the same direction as the input shaft when the housing is in a second position.

In accordance with the first aspect, the output gear may be coupled with the input gear to couple the output shaft with the input shaft when the housing is in the first position. The idler gear may be coupled with the output gear and the input gear to couple the output shaft, the idler shaft, and the input shaft when the housing is in the second position. The input shaft, the output shaft and the idler shaft may be parallel to each other. The input gear, output gear and the idler gear may be axially located helical gears.

In accordance with this aspect, a proximal end of the input shaft may be attached to the housing by a first spring such that the input gear is pushed towards a distal end of the housing. The input gear may be housed in a first chamber, the idler gear may be housed in a second chamber and the output gear may be housed in a third chamber.

In a second aspect of the present invention, there is provided a gear shifter. The gear shifter may include a housing, an input shaft, an output shaft and an idler shaft. The input shaft may include a pair of input gears. A first side of the input shaft may be within the housing and a second side of the input shaft may extend from the housing. The output shaft may have a pair of output gears. A first side of the output shaft may be within the housing and a second side of the output shaft may extend from the housing. The idler shaft may have a pair of idler gears and the first idler gear may be coupled to the first input gear. The output shaft may be slidably coupled with the input shaft and may rotate in an opposite direction of the input shaft when the housing is in a first position. The output shaft may be slidably coupled with the idler shaft and may rotate in the same direction as the input shaft when the housing is in a second position.

In accordance with the second aspect, a first output gear may be coupled with the second input gear to couple the output shaft with the input shaft when the housing is in the first position. A second output gear may be coupled with a second idler gear to couple the output shaft with the idler shaft when the housing is in the second position. The input shaft, the output shaft and the idler shaft may be parallel to each other. The input gears, output gears and idler gears may be axially located helical gears.

In accordance with this aspect, the output shaft may consist of an outer shaft disposed over an inner shaft. The inner shaft may be coaxial to the outer shaft and extend from the outer shaft in a distal and a proximal direction. The output shaft and the input shaft may rotate independent of each other. The output shaft may have external helical threading on a distal end. The distal end of the inner shaft may be a screw engaging surface. The screw engaging surface may be configured to interface with a pedicle screw head.

In accordance with this aspect, a proximal end of the inner shaft may be attached to the housing by a first spring, and a proximal end of the outer shaft may be attached to the housing by a second spring such that the input gears are pushed towards a distal end of the housing. The input gears may be housed in a first chamber, the idler gears may be housed in a second chamber and the output gears may be housed in a third chamber.

A third aspect of the present invention is a method of reversing an output shaft direction using a gear shifter. A method in accordance with this aspect may include the steps of pushing the gear shifter in a first direction and pushing the gear shifter in a second direction. Pushing the gears shifter in the first direction may rotate the output shaft in a first direction and pushing the gear shifter in the second direction may rotate the gear shifter in a second direction.

A fourth aspect of the present invention is a method of inserting a pedicle screw. A method in accordance with this aspect may include the steps of engaging an output shaft of a gear shifter with a pedicle screw with the gear shifter in a first position, inserting the pedicle screw in a pedicle of a vertebral body with the gear shifter remaining in the first position, moving the gear shifter to a second position and disengaging the output shaft from the pedicle screw with the gear shifter in the second position. The gear shifter may be moved from the first position to the second position in the same direction as the disengagement of the output shaft from the pedicle screw.

A fifth aspect of the present invention is a method of reversing an output shaft direction using a gear shifter wherein the output shaft is driven by a unidirectional input shaft. A method in accordance with this aspect may include the steps of attaching the input shaft to a first end of the gear shifter, attaching the output shaft to a second end of the gear shifter, pushing the gear shifter in a distal direction to rotate the output shaft in a first direction, and pushing the gear shifter in a proximal direction to rotate the output shaft in a second direction. The gear shifter may include a pair of input gears on the input shaft, a pair of idler gears on an idler shaft, and a pair of output gears on the output shaft. The input shaft may rotate in a counterclockwise direction. The step of pushing the gear shifter in distal direction may rotate the input shaft in a clockwise direction. The step of pushing the gear shifter in a proximal direction may rotate the input shaft in counterclockwise direction.

In accordance with this aspect, the output shaft may be a pedicle screwdriver with an outer shaft having external threads at a distal end. The outer shaft may be disposed around an inner shaft. The inner shaft may be coaxial to the outer shaft and extend from the outer shaft in a distal and a proximal direction. The inner shaft may have a screw engaging distal end. The step of pushing the gear shifter in a distal direction may rotate the inner shaft in a clockwise direction to insert a pedicle screw into a vertebral body. The step of pushing the gear shifter in a proximal direction may rotate the outer shaft of the pedicle screwdriver to retract the pedicle screwdriver without rotating the inner shaft. The input shaft may be coupled to a robotic arm configured for robotic surgery.

BRIEF DESCRIPTION OF THE DRAWINGS

A more complete appreciation of the subject matter of the present invention and the various advantages thereof can be realized by reference to the following detailed descriptions, in which reference is made to the following accompanying drawings.

DETAILED DESCRIPTION

Figure 1:
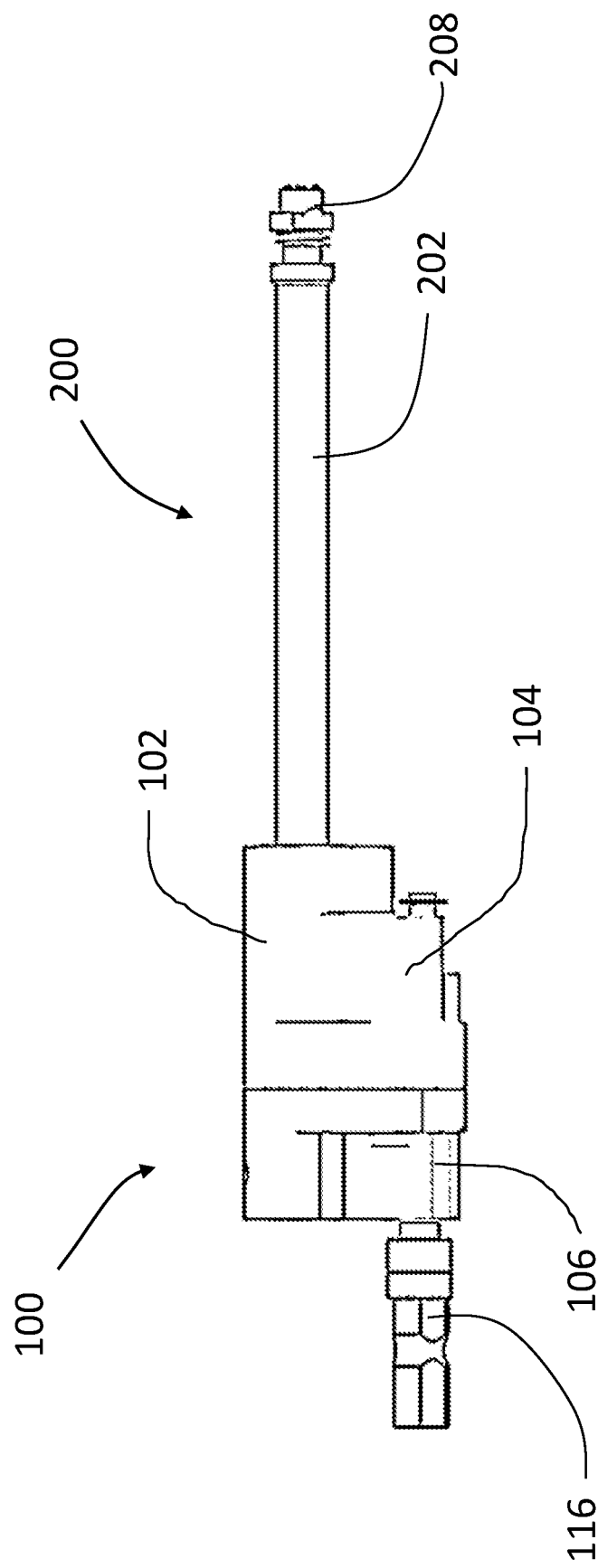
FIG. 1 is a side elevation view of a gear shifter for a pedicle screwdriver according to one embodiment of the present invention.
Figure 2:
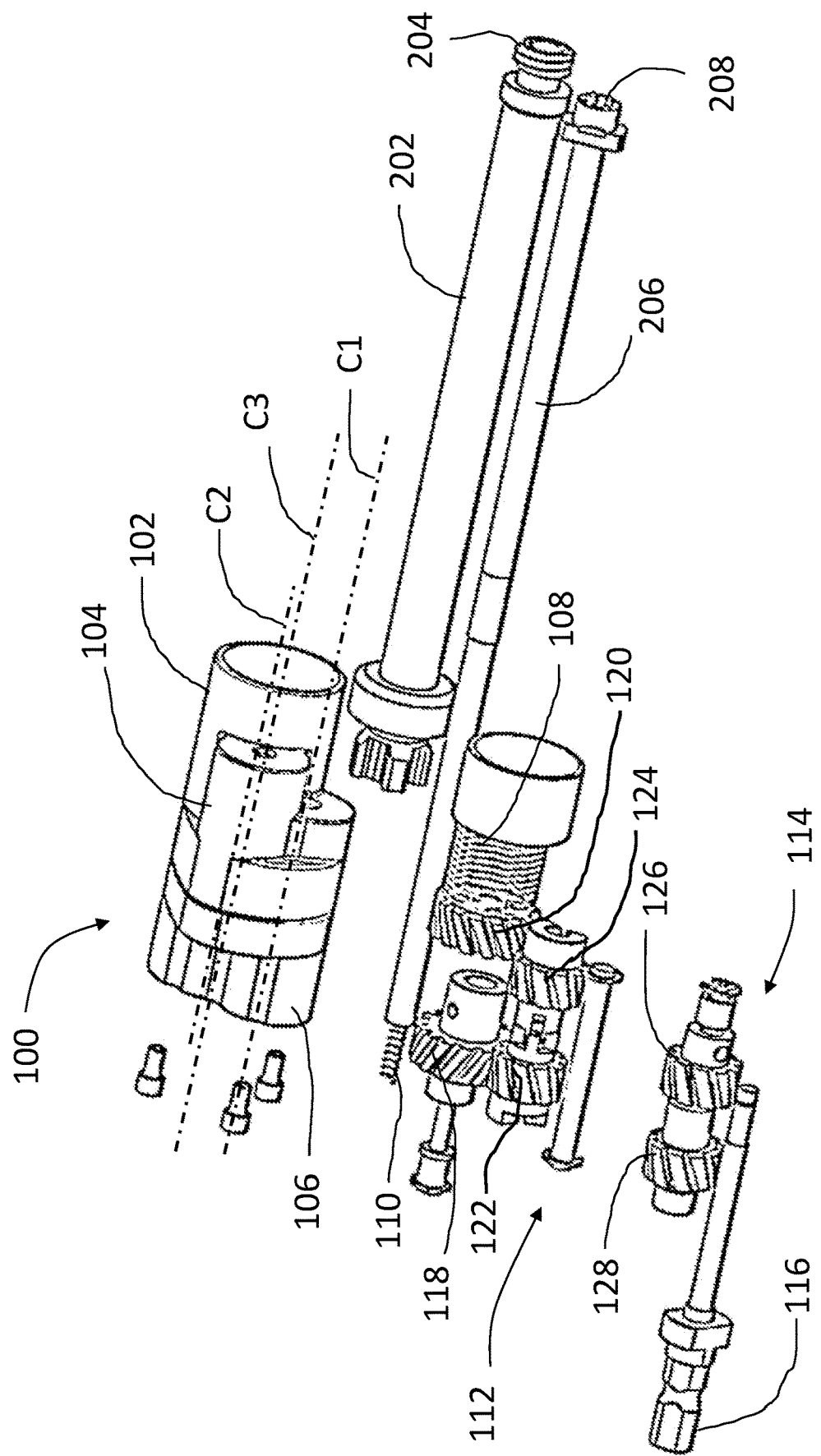
FIG. 2 is an exploded perspective view of the gear shifter shown in FIG. 1.

FIG. 1 depicts a power pedicle screwdriver 200 with a gear shifter 100 according to one embodiment of the present invention. Gear shifter 100 includes a housing structure with an input shaft chamber 106, an output shaft chamber 102, and an idler shaft chamber 104. The three cylindrical shaft chambers are parallel to each other as indicated by their respective central axes: C1, C2 and C3, as shown in FIG. 2. An input shaft 116 extends through one end of gear shifter 100, and pedicle screwdriver 200 extends through the opposite end.

FIG. 2 shows an exploded perspective view of the components of gear shifter 100 and power pedicle screwdriver 200. Input shaft chamber 102 houses an outer shaft 202 and an inner shaft 206 of pedicle screwdriver 200. Outer shaft 202 is disposed around inner shaft 206 allowing for each shaft to rotate independent of each other. For example, when outer shaft 202 rotates in a counterclockwise direction, inner shaft 206 may not rotate. A distal end of outer shaft 202 includes threads 204 configured to engage with a pedicle screw tulip or coupling element (shown in FIGS. 7A-7E), whereas the inner shaft's distal end has an engaging surface 208 for engaging with a screw portion of the pedicle screw. Coil springs 110 and 108 are provided on the proximal ends of the inner and outer shaft respectively. These coil springs force the inner and outer shaft against a distal end of input shaft chamber 102. Also housed in the input shaft chamber are two axially located helical gears 118 and 120 (best shown in FIG. 3) which control the inner and outer shaft rotation of pedicle screw driver 200 as more fully explained below. Idler shaft chamber 104 includes an idler shaft 112 and two axial helical gears 122 and 124. Input drive shaft 114 extends from a proximal end 116 of input shaft chamber 106, and has two axially located helical gears 126 and 128.

Figure 3:
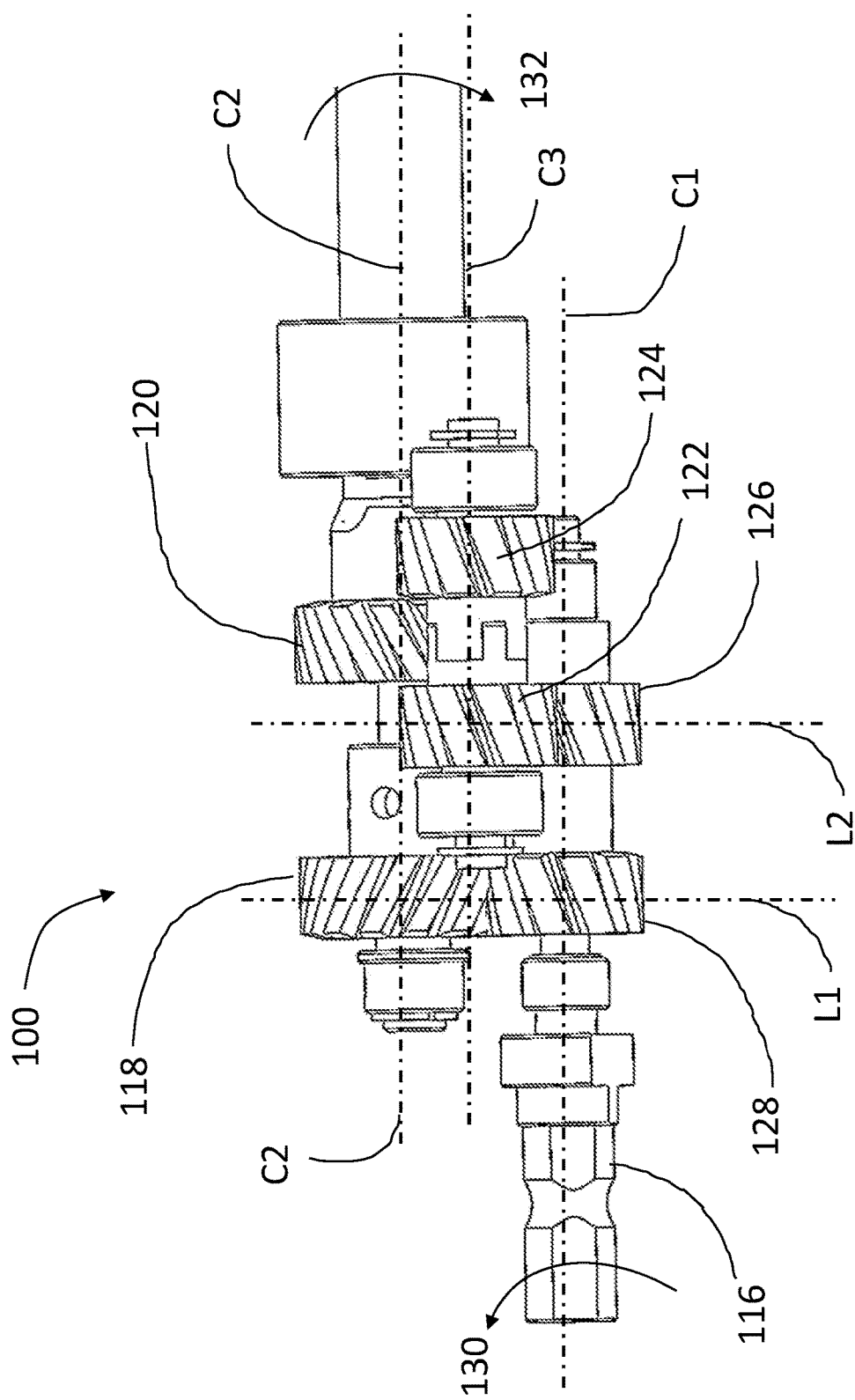
FIG. 3 is a side elevation view showing an internal gearing arrangement according to a first position of the gear shifter shown in FIG. 1.

A side elevation view of the internal gearing according to a first position of gear shifter 100 is shown in FIG. 3. In this first position, helical gear 118 located on inner shaft 206 of the pedicle screwdriver and helical gear 128 of input shaft 116 lie on a common longitudinal axis L1 and are coupled to each other. Helical gear 120 on outer shaft 202 of pedicle screwdriver 200 is disengaged from all other gears. Although idler gear 122 is coupled to helical gear 126 of input shaft 116 in this first position, output shaft members (inner and outer shaft of pedicle screwdriver 200) remain disengaged from both idler gears 122 and 124. When input shaft rotates in a counterclockwise direction as indicated by direction arrow 130, helical gear 118 turns in a clockwise direction indicated by direction arrow 132, thereby moving inner shaft 206 of pedicle screwdriver 200. In this embodiment, outer shaft 202 also rotates with the inner shaft to ensure that the outer shaft remains engaged with a coupling element of a pedicle screw during insertion. Other embodiments may not require the outer shaft to rotate with the inner shaft. Therefore, in this first position of gear shifter 100, an input shaft rotating in a counterclockwise direction turns an output shaft in a clockwise direction.

Figure 4:
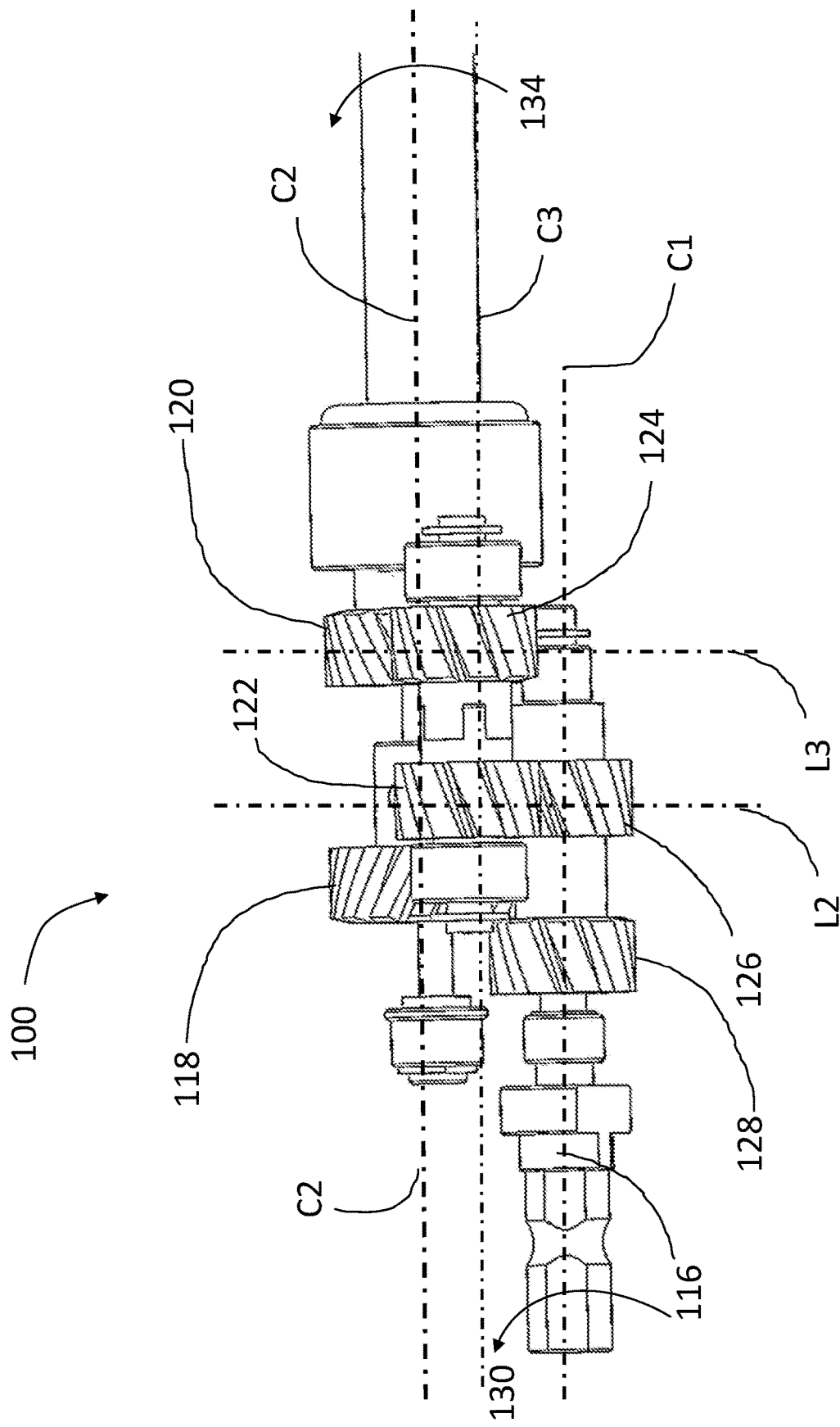
FIG. 4 is a side elevation view showing an internal gearing arrangement according to a second position of the gear shifter shown in FIG. 1.

Referring now to FIG. 4, a side elevation of the internal gearing according to a second position of gear shifter 100 is shown. Helical gear 118 of output shaft (inner shaft 206) is disengaged in this position. Idler gear 124 and helical gear 120 of output shaft (outer shaft 202) lie on the same longitudinal axis L3 and are coupled. Idler gear 122 and input shaft gear 126 also lie on a common longitudinal axis L2 and are also coupled in this second position. As shown in the first position, input shaft 116 continues to rotate in a counterclockwise direction. However, the engagement of the idler gears results in the output shaft (outer shaft 202) rotating in the same direction as the input shaft in this second arrangement (depicted with arrow 134).

Figure 5A:
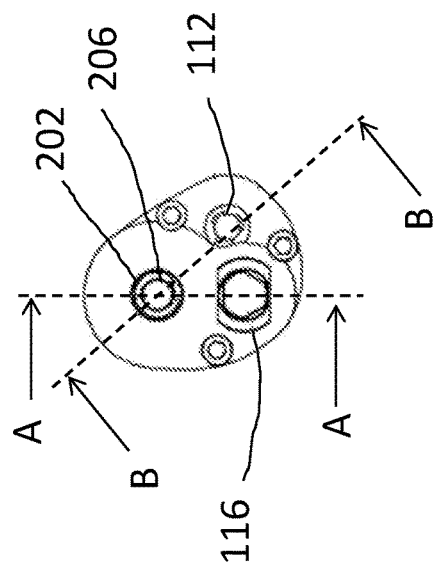
FIG. 5A is a front view of the gear shifter of FIG. 1.
Figure 5B:
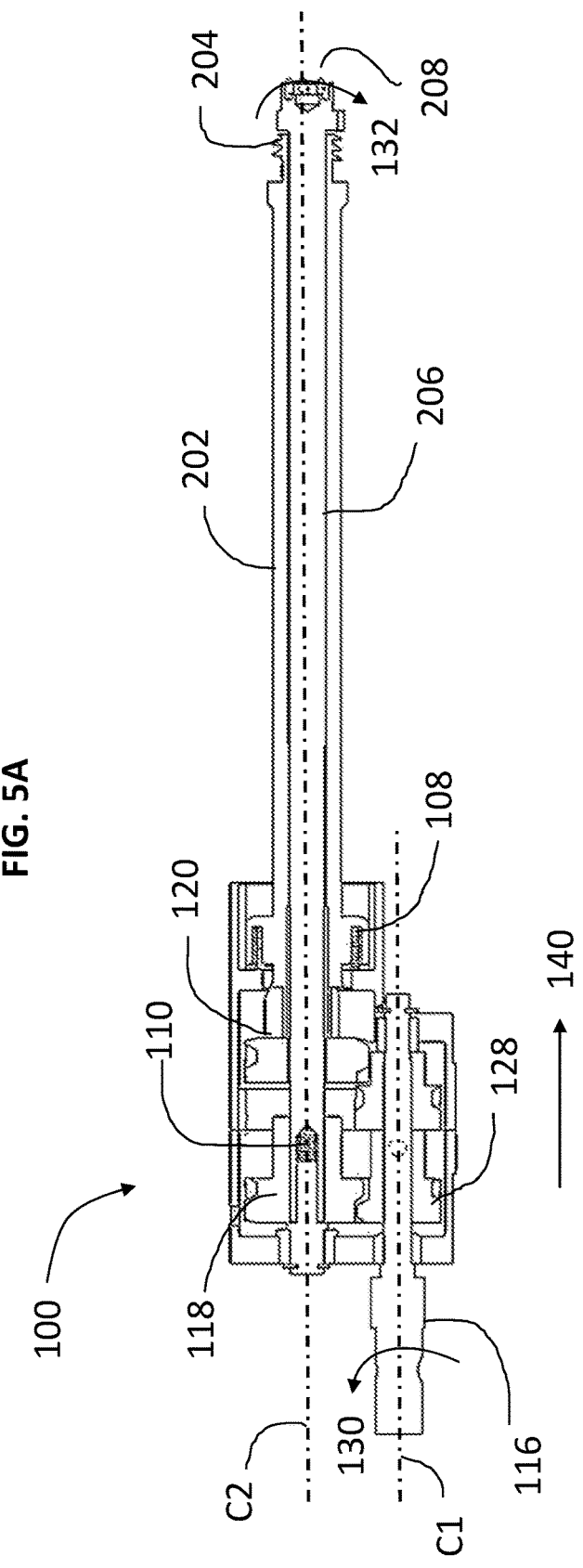
FIG. 5B is a cross-sectional elevation view taken along line A-A of FIG. 5A showing an interior of the gear shifter housing in the first position shown in FIG. 3.

A cross-sectional view of gear shifter 100 through line A-A of FIG. 5A is shown in FIG. 5B. When the gear shifter is pushed toward the distal end of the pedicle screw driver as shown by direction arrow 140, helical gears 118 and 128 align along a common longitudinal axis L1 as is discussed above in connection with FIG. 3. Coil springs 110 and 108 attached to the inner and outer shaft of pedicle screwdriver 200 respectively are compressed because the inner and outer shafts are pushed against the proximal end of input shaft chamber 102. As described above, counterclockwise rotation of input shaft 116 will rotate inner shaft 206 of pedicle screw driver 200 in a clockwise direction when gear shifter 100 is set in this first position.

Figure 5C:
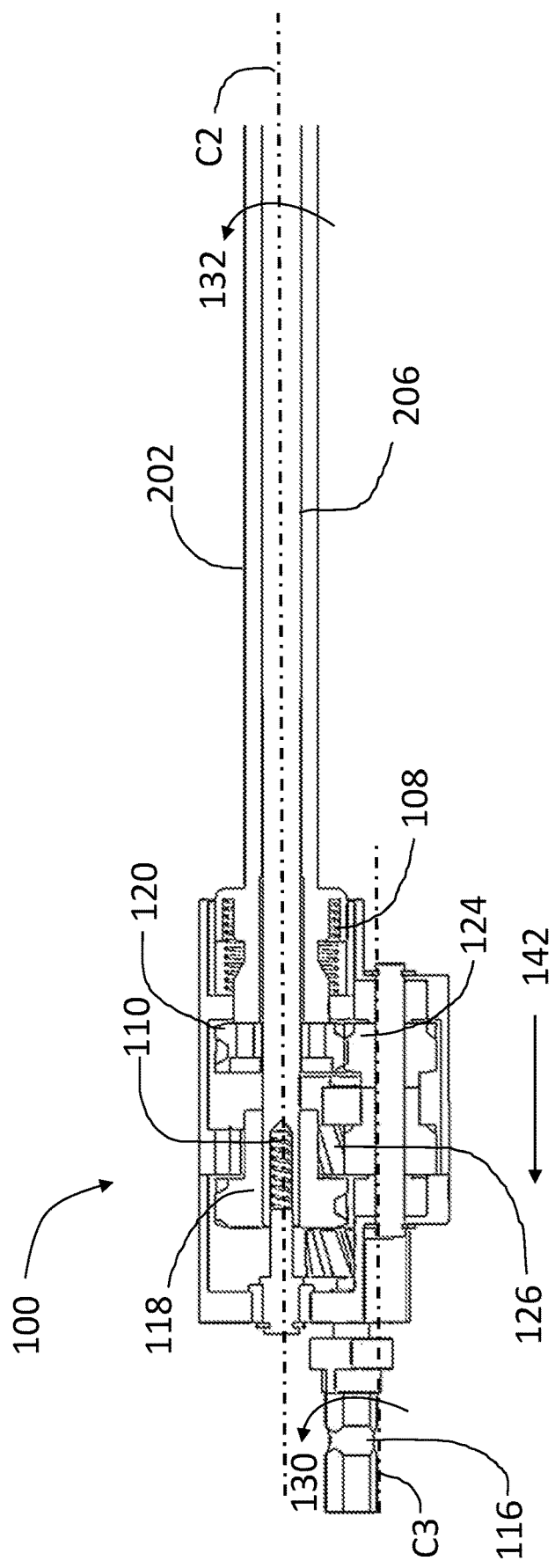
FIG. 5C is a cross-sectional elevation view taken along line B-B of FIG. 5A showing an interior of the gear shifter housing in the second position shown in FIG. 4.

FIG. 5C is a cross-sectional view of gear shifter 100 through line B-B of FIG. 5A. Pulling gear shifter 100 in the opposite second direction as indicated by direction arrow 142 results in helical gears 120 and 124 aligning along the common longitudinal axis L3, as is discussed above in connection with FIG. 4. Coil springs 110 and 108 are uncompressed or less compressed than they are in the first position when gear shifter is set in the second position. The counterclockwise rotation of input shaft 116 will now rotate outer shaft 202 in a counterclockwise direction. Inner shaft 206 of pedicle screwdriver 200 does not rotate when gear shifter 100 is set in the second position. Although helical gears are shown in the current embodiment, other suitable gears may be used in other embodiments. In other embodiments, the reverse gear shifter may have only one idler gear on the idler shaft coupled to the input and output shaft in the second position to rotate input and output shafts in the same direction. While the input shaft in this embodiment has an inner and outer shaft, other embodiments may only have a single output shaft with a single output gear.

Figure 6:
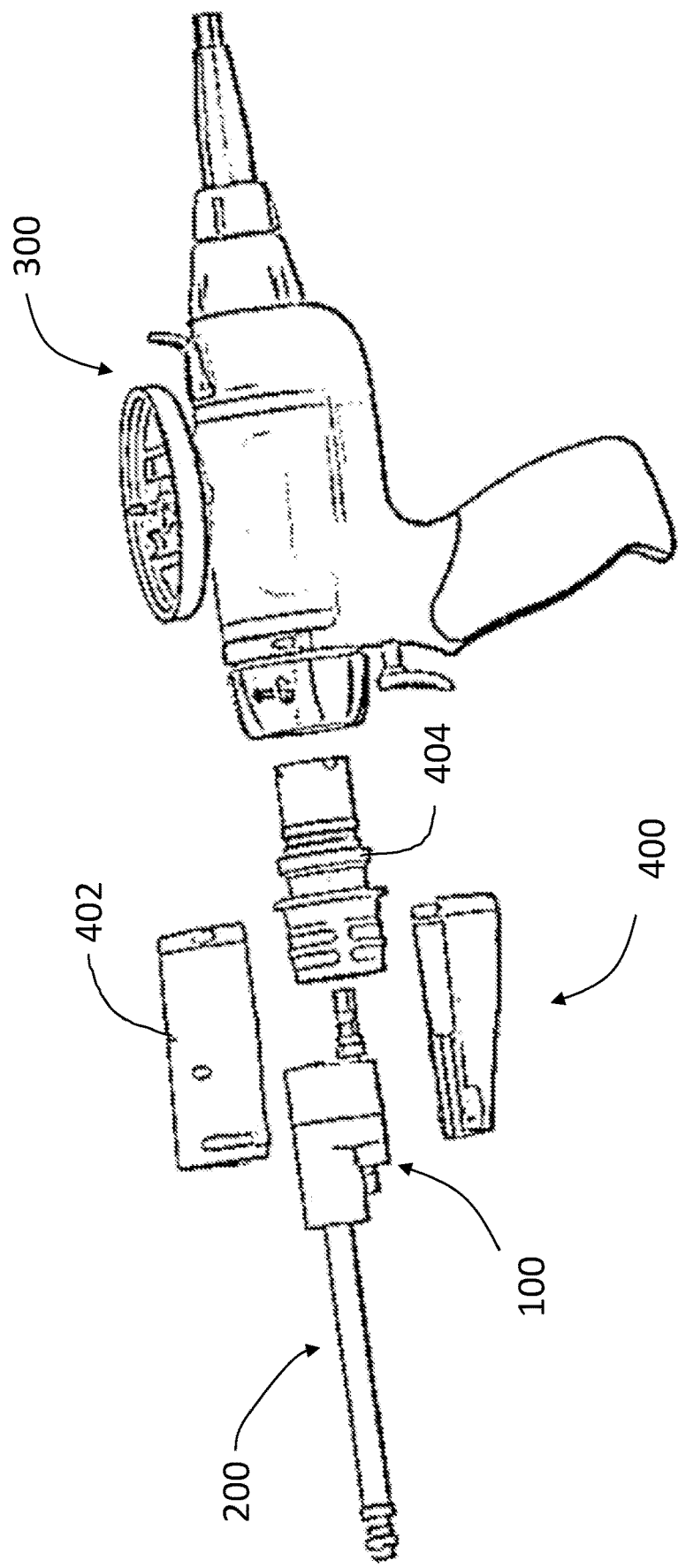
FIG. 6 is a perspective view of the gear shifter of FIG. 1 in conjunction with a pedicle screwdriver and associated robotic arm.

Referring now to FIG. 6, there is shown gear shifter 100 and power pedicle screw driver 200 in conjunction with attachment components 400 for a hand piece 300 which may be attached to a robotic arm (not shown). Attachment components shown in this embodiment include two connection pieces 402 and a reamer adaptor 404. Other embodiments may include different attachment components or may be directly attached to a hand piece.

Figure 7B:
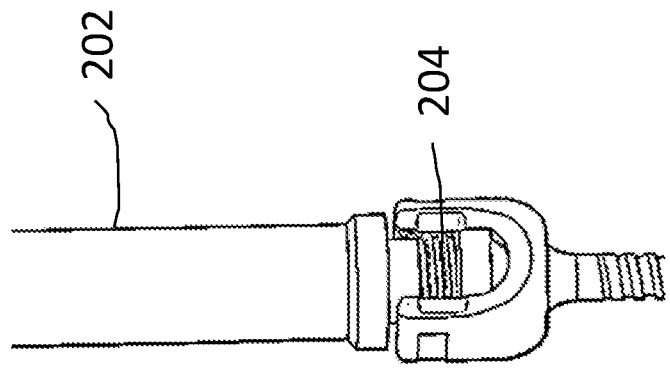
FIGS. 7A-7E depict attachment of a pedicle screw to the gear shifter shown in FIG. 1, insertion of the pedicle screw into a pedicle and retraction of the gear shifter from the pedicle screw.
Figure 7A:
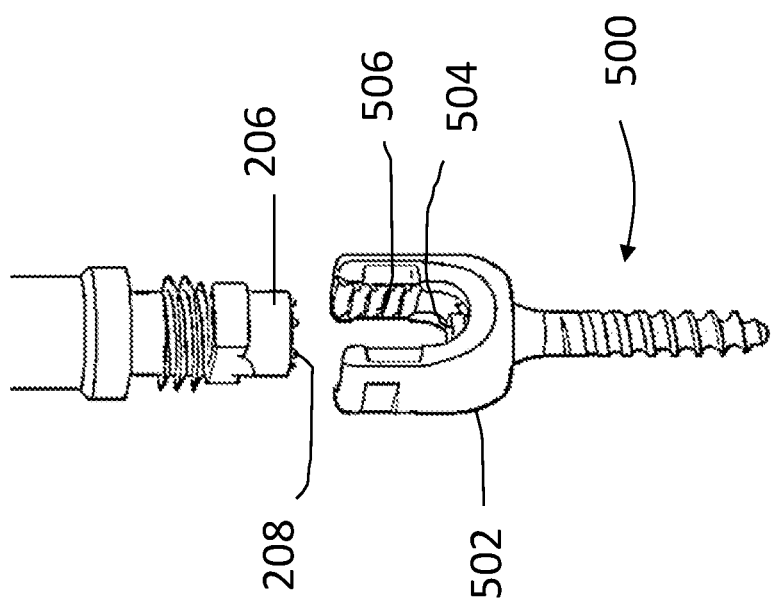
Figure 7D:
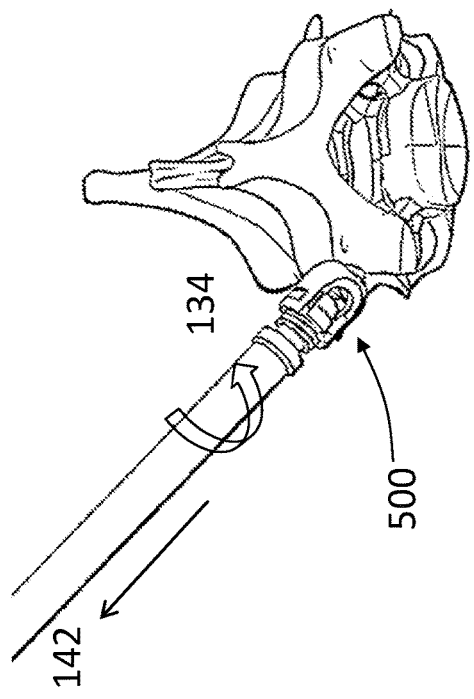
Figure 7E:
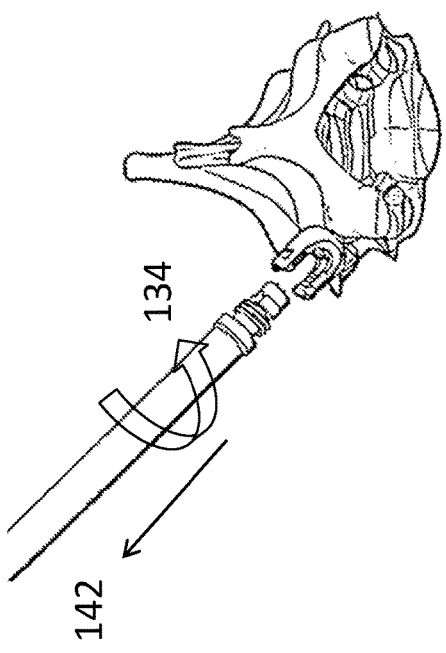

In a method according to a further aspect of the present disclosure, steps to insert a pedicle screw 500 into a vertebral body 600 with gear shifter 100 and power pedicle screwdriver 200 are shown in FIGS. 7A-7E. Threads 204 on the distal end of outer shaft 202 are first coupled with corresponding threads 506 present on the inner surface of coupling element 502 of pedicle screw 500 as best shown in FIGS. 7A and 7B. Pedicle screw engaging surface 208 securely fits into pedicle screw head 504 when outer shaft 202 is fully screwed into coupling element 502. Pedicle screw engaging surface of power pedicle screwdriver 200 may include conical, cylindrical, tapered, hollow or other similar surfaces configured to engage with corresponding recesses or projections on pedicle screw head 504. For instance, the pedicle screw engagement surfaces may take on any of the designs disclosed in U.S. Pat. No. 8,231,635, the disclosure of which is hereby incorporated by reference herein, among others. The outer shaft connection with the pedicle screw coupling element ensures that the pedicle screwdriver does not prematurely disengage before the pedicle screw is properly inserted on vertebral body 600.

Figure 7C:
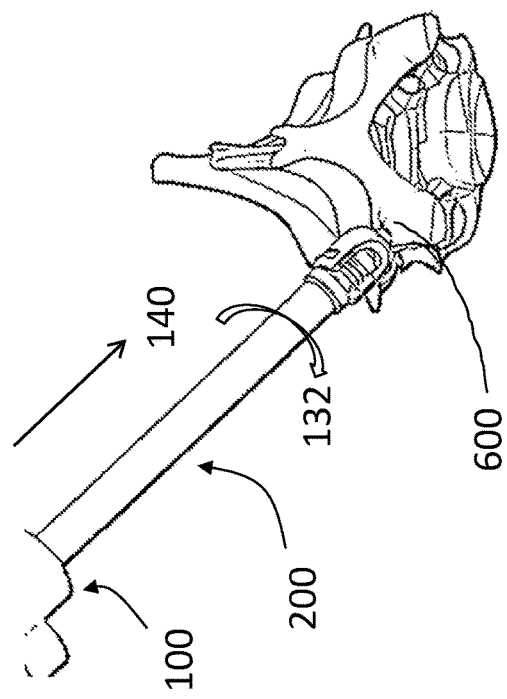

Gear shifter 100 automatically falls into the first position when either the gear shifter housing or the outer shaft of pedicle screwdriver 200 is manually pushed towards the bone. As more fully explained above, setting gear shifter 100 in the first position will rotate inner shaft 208 in a clockwise direction as shown in FIG. 7C. Coil springs 110, 108, and the three gear shifter chambers are configured to allow an operator to change gear shifter setting with minimal effort. Pedicle screwdriver 200 is pushed down toward the vertebral body as indicated by direction arrow 140 to begin pedicle screw 500 insertion at the desired location on vertebral body 600. Once pedicle screw 500 is fully secured, the operator may pull gear shifter 100 of pedicle screwdriver 200 away from the vertebral body 600 as shown by direction arrow 142 in FIG. 7D to set gear shifter 100 in the second position. In other embodiments, the outer shaft of pedicle screwdriver 200 may be used to set gear shifter 100 in the second position by pulling the outer shaft away from the vertebral body. Minimal effort is once again required to switch gear shifter 100 from the first to the second position and can be manually done by the operator during surgery. As more fully described above, outer shaft 202 rotates in a counterclockwise direction, whereas the inner shaft does not rotate in the second position. This allows the outer shaft to unscrew and disengage from the coupling element 502 of pedicle screw 500 without disturbing pedicle screw head 504 because inner shaft is retracted away from the screw without rotation. The two gear shift positions, i.e., pushing towards the vertebra to insert pedicle screw, and pulling away from the bone to retract pedicle screwdriver, provide the operator with both tactile and visual confirmation during insertion of the pedicle screw and retraction of the pedicle screwdriver. Because the operator may push and hold the gear shifter in the direction of insertion or retraction while preforming these respective steps, the operator receives continuous tactile feedback throughout the surgical procedure, and consequently reduces operator error in selecting the correct mode, i.e., insertion or retraction. While a pedicle screwdriver and pedicle screw insertion procedure is described in this embodiment, other embodiments may include other medical or non-medical components combined with the gear shifter of the present invention.

The gear shifter of the present disclosure may be fabricated using aluminum alloy 6061 for the gear shifter housing, stainless steel for the shafts, and material with a low coefficient of friction such as PEEK for the bushing. Other suitable materials may also be used to fabricate any of the components of the present disclosure without departing from the scope of the present invention. Whereas the present disclosure describes a gear shifter with two gears on each shaft (output, idler, input), other embodiments may include only a single gear on each shaft to perform the same function(s). Gear sizes and shapes can also be varied in other embodiments. Output, input and idler shafts may also be arranged differently in conjunction with corresponding alternative configurations of springs and housing structures in other embodiments. Therefore, the overall shape and size of the gear shifter of the present invention may vary widely depending on the application.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A method of inserting a pedicle screw comprising the steps of:
   engaging an inner shaft and an outer shaft of an output shaft assembly of a gear shifter with a pedicle screw, the outer shaft being disposed around the inner shaft, a proximal end of the output shaft assembly being coupled to an input shaft within a gear shifter housing;
   moving the gear shifter to a first position by sliding the gear shifter housing across the output shaft assembly and toward the pedicle screw to rotate the inner shaft in a first direction;
   inserting the pedicle screw in a pedicle of a vertebral body, with the gear shifter remaining in the first position;
   moving the gear shifter to a second position by sliding the gear shifter housing across the output shaft assembly and away from the pedicle screw to rotate the outer shaft in a second direction opposite to the first direction, and
   disengaging the inner shaft and the outer shaft from the pedicle screw, with the gear shifter in the second position.

2. The method of claim 1, wherein the gear shifter is moved from the first position to the second position in the same direction as the disengagement of the inner shaft and the outer shaft from the pedicle screw.

3. The method of claim 1, wherein the inner shaft and outer shaft are driven by the input shaft, the input shaft being a unidirectional input shaft.

4. The method according to claim 3, wherein the gear shifter comprises of a pair of input gears on the input shaft, a pair of idler gears on an idler shaft and a pair of output gears on the output shaft assembly, the input gears, the idler gears and the output gears being disposed within the gear shifter housing.

5. The method according to claim 4, wherein the input shaft is coupled to a handpiece, the handpiece configured to be attached to a robotic arm configured for robotic surgery.

6. The method according to claim 3, wherein the output shaft assembly is a pedicle screwdriver with the outer shaft having external threads at a distal end, the inner shaft being coaxial to the outer shaft and extending from the outer shaft in a distal and a proximal direction, the inner shaft having a pedicle screw engaging distal end.

7. The method according to claim 6, wherein the inner shaft rotates in a clockwise direction to insert the pedicle screw into the vertebral body in the first position.

8. The method according to claim 6, wherein the step of moving the gear shifter to the second position rotates the outer shaft of the pedicle screwdriver to retract the pedicle screwdriver without rotating the inner shaft.

9. The method according to claim 6, wherein the input shaft rotates in a clockwise direction in the first position.

10. The method according to claim 6, wherein moving the gear shifter to the second position rotates the input shaft in a counterclockwise direction.

11. A method of inserting a bone screw comprising the steps of:
    engaging an inner shaft and outer shaft of an output shaft assembly of a gear shifter with a bone screw, the outer shaft being disposed around the inner shaft, a proximal end of the output shaft assembly being coupled to an input shaft within a gear shifter housing;
    moving the gear shifter to a first position by sliding the gear shifter housing across the output shaft assembly and toward the bone screw to rotate the inner shaft in a first direction;
    inserting the bone screw into a target surgical site, with the gear shifter remaining in the first position;
    moving the gear shifter to a second position by sliding the gear shifter housing across the output shaft assembly and away from the bone screw to rotate the outer shaft in a second direction opposite to the first direction, and
    disengaging the inner shaft and the outer shaft from the bone screw, with the gear shifter in the second position.

12. The method of claim 11, wherein the gear shifter is moved from the first position to the second position in the same direction as the disengagement of the inner shaft and the outer shaft from the bone screw.

13. The method of claim 11, wherein the outer shaft and the inner shaft are driven by the input shaft, the input shaft being a unidirectional input shaft.

14. The method according to claim 13, wherein the gear shifter comprises of a pair of input gears on the input shaft, a pair of idler gears on an idler shaft and a pair of output gears on the output shaft assembly, the input gears, the idler gears and the output gears being disposed within the gear shifter housing.

15. The method according to claim 14, wherein the input shaft is coupled to a handpiece, the handpiece configured to be attached to a robotic arm configured for robotic surgery.

16. The method according to claim 13, wherein the output shaft assembly is a bone screwdriver with the outer shaft having external threads at a distal end, the inner shaft being coaxial to the outer shaft and extending from the outer shaft in a distal and a proximal direction, the inner shaft having a bone screw engaging distal end.

17. The method according to claim 16, wherein the inner shaft rotates in a clockwise direction to insert the bone screw into the surgical site in the first position.

18. The method according to claim 16, wherein the step of moving the gear shifter to the second position rotates the outer shaft of the bone screwdriver to retract the bone screwdriver without rotating the inner shaft.

19. The method according to claim 16, wherein the input shaft rotates in a clockwise direction in the first position.

20. The method according to claim 16, wherein moving the gear shifter to the second position rotates the input shaft in a counterclockwise direction.

* * * * *